(12) United States Patent
Blagg

(10) Patent No.: US 12,029,872 B2
(45) Date of Patent: Jul. 9, 2024

(54) INSECT REPELLENT AND SUNSCREEN APPLICATOR

(71) Applicant: Mary Diane Blagg, Hot Springs, AR (US)

(72) Inventor: Mary Diane Blagg, Hot Springs, AR (US)

(*) Notice: Subject to any disclaimer, the term of this patent is extended or adjusted under 35 U.S.C. 154(b) by 3 days.

(21) Appl. No.: 17/511,172

(22) Filed: Oct. 26, 2021

(65) Prior Publication Data

US 2022/0184363 A1 Jun. 16, 2022

Related U.S. Application Data

(60) Provisional application No. 63/123,713, filed on Dec. 10, 2020.

(51) Int. Cl.
*A61M 35/00* (2006.01)
*A45D 34/04* (2006.01)

(52) U.S. Cl.
CPC ........... *A61M 35/006* (2013.01); *A45D 34/04* (2013.01); *A45D 2200/1018* (2013.01); *A61M 2205/025* (2013.01)

(58) Field of Classification Search
CPC ................ A61M 35/006; A61M 35/00; A61M 2205/025; A45D 34/04; A45D 2200/1018
USPC ....................................................... 604/310
See application file for complete search history.

(56) References Cited

U.S. PATENT DOCUMENTS

| 1,318,256 | A | | 10/1919 | Birsan |
| 1,532,830 | A | | 4/1925 | Marceau |
| 1,553,049 | A | | 9/1925 | Romero |
| 1,818,340 | A | | 8/1931 | Lemoine |
| 2,919,703 | A | | 1/1960 | Pinteau |
| 3,466,131 | A | | 9/1969 | Arcudi |
| 3,704,072 | A | | 11/1972 | Kaufman |
| 4,148,318 | A | | 4/1979 | Meyer |
| 4,269,527 | A | | 5/1981 | Lipfert |
| 4,557,620 | A | | 12/1985 | Hancy |
| 4,617,875 | A | | 10/1986 | Holland |
| 5,019,033 | A | | 5/1991 | Geria |
| 5,636,931 | A | * | 6/1997 | Gueret ............... A46B 11/0017 401/129 |
| 5,865,194 | A | | 2/1999 | Gueret |

(Continued)

*Primary Examiner* — Andrew J Mensh
(74) *Attorney, Agent, or Firm* — Stephen D. Carver

(57) ABSTRACT

A portable applicator for uniformly applying insect repellent or sunscreen upon human skin. A jar-like container normally holds the liquid contents. The container is sealed by a circular lid. The lid supports a downwardly-projecting sponge wiper that is saturated with liquid for subsequent topical application. The underside of the lid has a glue area surrounded by a peripheral ring for securing the wiper, and channels for directing fluid. A wringer-saturator, in the form of a foraminous partition, is disposed between the applicator contents and the wiper. When the applicator is closed, the wiper is compressed slightly by contact with the wringer-saturator. As the lid is removed from the container, the wiper will expand slightly, absorbing and holding liquid. When the lid is reattached, the wiper is compressed slightly against the wringer-saturator and liquid is partially expelled. The wiper has a fiberglass fabric covering for preventing dripping and easing topical application.

5 Claims, 10 Drawing Sheets

(56) References Cited

U.S. PATENT DOCUMENTS

| | | | | |
|---|---|---|---|---|
| 6,009,885 | A | * | 1/2000 | Nam ................... A45D 33/006 |
| | | | | 132/305 |
| 6,068,880 | A | * | 5/2000 | Hills ....................... B05D 1/12 |
| | | | | 427/180 |
| 7,201,525 | B2 | | 4/2007 | Mohiuddin |
| 7,726,322 | B2 | * | 6/2010 | Cho .................... A45D 33/006 |
| | | | | 132/294 |
| 7,866,907 | B2 | | 1/2011 | Cable |
| 8,651,119 | B2 | | 2/2014 | Byun |
| 2002/0112738 | A1 | * | 8/2002 | Parker .................. A61M 35/25 |
| | | | | 132/333 |
| 2007/0206986 | A1 | * | 9/2007 | Gueret ............... A61H 23/0263 |
| | | | | 401/123 |
| 2013/0118521 | A1 | * | 5/2013 | Byun .................... A46B 9/021 |
| | | | | 132/294 |
| 2016/0128447 | A1 | * | 5/2016 | Lim ...................... A45D 40/18 |
| | | | | 132/317 |

* cited by examiner

INSECT REPELLENT AND SUNSCREEN APPLICATOR

CROSS-REFERENCE TO RELATED APPLICATION

This utility patent application is based upon and claims priority from previously filed and currently Provisional Patent Application Ser. No. 63/123,713, filed Dec. 20, 2020, and entitled "Insect Repellent and Sunscreen Applicator," both by inventor Mary Diane Blagg, an American Citizen, and priority is claimed from said provisional filing.

BACKGROUND OF THE INVENTION

I. Field of the Invention

The present invention relates to applicators for the safe and efficient topical application of bug and insect repellents, and sunscreens. More particularly, the present invention relates to liquid repellent applicators of the type comprising a closed system container, a removable closure, and skin contacting structure secured to the closure for absorbing and then applying liquid repellent to the human skin. Prior art germane to the invention can be found in United States Patent Classes 132 and 401.

II. Description of the Prior Art

It is well recognized that certain annoying insects, such as mosquitoes, can transmit various diseases such as malaria. Insect repellents protect human health by minimizing the transmission of germs and viruses that can transmit Lyme disease, Zika, the West Nile virus, encephalitis, malaria, and the serious Alphagal syndrome, which is a recently identified type of food allergy that most often begins when a Lone Star tick bites someone. The bite transmits a sugar molecule called "alpha-gal" into the person's body. Lyme disease is spread by tick bites. Pest insects have long been carriers and spreaders of diseases as they not only feed on animals, but on humans as well.

In North America, mosquitoes, ticks, and black flies are the three major groups of arthropods pestiferous to humans. While black flies and mosquitoes in North America are primarily a nuisance, a tick bite can be more serious. In particular, significant attention in the northeast United States recently has been focused upon the Lyme disease ticks (*Ixodes damini*) which have spread in geographical area as well as in number, and which carry the potentially debilitating Lyme disease. Similarly, in warmer climates such as Latin America, a serious and potentially fatal malady known as Chagas' disease are carried by triatomes (Chagas bugs) which are active at night and feed on people as they sleep. In Africa, mosquitoes carry malaria. It has been suggested, although yet unproven, that the recently ubiquitous Covid 19 disease may also be spread by insects including mosquitoes.

CDC scientists analyzed data reported to the National Notifiable Diseases Surveillance System for sixteen vector-borne diseases from 2005 to 2020 to identify trends. Many infections are not reported or recognized, so it has been difficult to accurately estimate the overall cost and burden of these diseases. In 2016 the most common tick-borne diseases in the U.S. were Lyme diseases and ehrlichosis/anaplasmosis. The most common mosquito-borne diseases were West Nile virus, dengue fever, and Zika. The increases in diseases caused by mosquitoes, ticks, and/or fleas in the U. S. is due to many factors. These insects are spreading beyond their former geographic boundaries increasing he likelihood of exposure to diverse populations. Overseas travelers can be infected unknowingly with a mosquito-transmitted disease like Zika, and then carry it back home. In addition, transmissions of previously unrecognized germs has occurred. Mosquitoes and ticks can spread viruses in the same manner that travelers subjected to the SARS and Corona or Covid-19 viruses contaminate others. By nature, if unconstrained, vector-borne viruses and diseases will only worsen without treatment.

Recent studies concluded that approximately one million cases of disease caused by mosquitoes, ticks or fleas were reported in the U. S. from 2005 to 2020, and these diseases can cause debilitating neurological symptoms. Mosquitoes transit disease to more than 700 million persons annually. Arboviruses transmitted by mosquitoes cause considerable outbreaks of eastern equine encephalitis, western equine encephalitis, St. Louis encephalitis, and La Cross encephalitis.

One increasingly common medical condition transmitted by ticks is "alpha-gal syndrome," which is a type of food allergy to red meat and other products made from mammals. In the United States this condition most often begins after a bite from a Lone Star tick. The bite transmits a sugar molecule called alpha-gal into the body of the victim. In some people this triggers an immune response reaction that later produces mild to severe allergic reactions to red meat such as beef, port or lamb and other animal products. The Lone Star tick that has previously bitten an animal is exposed to the alph-gal sugar molecule, and transfers it to the next bitten animal or human. The Lone Star tick is found mostly in the Southeastern United States, where most cases of alpha-gal syndrome are reported. The tick is also found in the eastern and south central regions of the United States. The condition is also being detected in the northern and western regions of the country, as deer carry the tick to new places. Alpha-gal syndrome also has been diagnosed in Europe, Australia and Asia where other types of ticks are responsible. Researchers now believe that some people who have frequent unexplained anaphylactic reactions, and who test negative for other food allergies may also be infected with the alpha-gal syndrome. There is no known treatment other than avoiding red meat and other mammalian-derived food products.

Furthermore, in the fall of 1999, the west Nile virus transmitted by mosquitoes, were detected for the first time in the Western Hemisphere. In the New York City area, sixty-two persons infected with the West Nile virus were hospitalized, and seven persons died. The CDC estimates that more than 2000 persons were infected with the West Nile virus in the year 2000. The virus has now been detected in twenty seven states, and it continues to spread. As recently as 2017 a huge Zika outbreak inside Florida, affecting tourism. In the summer of 2019, mosquitoes carrying the Eastern Equine encephalitis virus threatened the northeastern United States and several people were infected.

According to The FDA, CDC, and Consumer Reports Magazine, studies have shown that natural repellent oils such as citronella, *eucalyptus*, lemon leaves, peppermint, lavender, and cedar and permethrin and various perfumed botanicals give limited protection, sometimes lasting for only one or two hours. Picaridin, which has been offered in the USA since 2005, is the most effective non-DEET repellent. Picaridin, also known as icaridin in the piperidine chemical family, is derived from the piper plant. It can be applied directly to skin or clothing. It has broad efficacy against various insects such as mosquitoes, ticks, gnats, flies and fleas, and is almost colorless and odorless. A study performed in 2010 showed that Picaridin spray and cream at a 20% concentration provided twelve hours of protection against ticks. Icaridin does not dissolve plastics, synthetics or sealants. While picaridin offers more repellent effectiveness that other botanicals, its fumes can burn or irritate the human eyes because it is based upon pepper extracts. Thus children should not be treated with picaridin.

DEET was developed for use in jungle warfare in the Pacific Theater in World War Two. The CDC, the U.S. Department of Health and Human Services, the NIH, the FDA, the EPA, the American Association of Pediatrics and the American Medical Association report that DEET, when properly used, is the safest and most effective repellent, exhibiting no contrary health indications after seventy-five years of use and testing. In the mid 1990's, and as recently as 2015, DEET was tested and found safe and non-carcinogenic. It is not a health risk to children and it can be used with children over two months old. It was deemed "safe" by the American Association of Pediatrics.

However, DEET-based products should not be overused on the skin or ingested. It is recommenced by the by the U. S. Department of Human Services and the CDC that fumes should not be inhaled or swallowed and eye contact must be avoided and it should not contact open wounds. Most recent DEET tests reveal that mixtures carrying in excess of 50% by volume yield diminishing returns. A twenty to forty percent concentration is ideal for nearly a full day of significant protection, with reapplication recommended after four to six hours. A seven percent concentration provides around two to three hours of protection. However, highly concentrated DEET mixtures can be worthwhile in dense forests and hot, humid jungle environments. The Entomological society of America and studies by American universities which received grants for insect repellent studies found that mosquitoes and ticks were strongly repelled by DEET mixtures, which functions for significant time periods.

The physical form of known repellents includes liquids, lotions, creams, sprays and the like. Spraying repellents requires going outdoors, resulting in streaks and necessitating rubbing and spreading with the hands. Lotions or creams generally require a user contact a large quantity of lotion on a hand and then wipe or rub it across all exposed skin to be protected. This requires the user to repeatedly place lotion on their hand for continued wiping, often resulting in an unwanted mess, inconvenience, and incomplete age; therefore typical users tends to omit reapplications. Almost one hundred percent protection from toxic bug bites and ultraviolet light can be acquired by correct application, involving the gentle rubbing and spreading of the product over exposed skin with the hands.

In general, repellent-laced clip-on products and other small attachment designs are generally ineffective beyond the immediate area around them. An effective DEET barrier is not obtained with these devices. In surveys it has been found that most users apply repellent hastily, if not haphazardly, with most omitting rubbing it over their skin evenly. In reality, some users grow impatient and omit bug repellent because of the trouble and inconvenience of conventional applicators, such as the irregular and imprecise age patterns of typical spray applicators, and the fear of breathing in fumes.

Many insect repellents are packaged in aerosol spray cans of typical commercial dimensions. Besides being bulky and generally inconvenient to carry, spray applicators often distribute repellent in an uneven manner, and often unintended targets are hit. Aerosol application problems may be acute when applying repellent to infants, or small children, and uncomfortable irritation may occur when spraying around the human face. Aerosol application is also disadvantageous because of the documented environmental consequences of aerosol Chloro Flouro Carbons ("CFC"). When an oily composition is sprayed upon the skin, the result is a greasy film which dries relatively slowly. When applying a more quick drying spray, it is difficult to produce a uniform coating. In order to coat the entire surface of an area of skin, it is necessary to liberally spray the entire area, often using an excessive volume of repellent, and wasting much of it.

Sunscreens are typically higher in viscosity than most insect-repellent liquid compositions. They are subject to strict CDC guidelines. It is recommended that sunscreens at a minimum of 15 SPF (i.e. "sun protection factor") should be applied every two hours. It takes only a few sunburn experiences for the risk of skin cancer to be increased demonstrably in later life, and severe melanoma can lead to loss of life. When engaging in outdoor activities requiring both insect repellent and sunscreens, the sunscreen is applied first and the repellent is applied afterwards.

Single use pre-moistened applicators contained in a compact, sealed package have been developed. Known commercial embodiments of such repellents include "wet-wipes". A wet wipe comprises a fabric-like article impregnated with a fluid, typically a surfactant and/or bactericide, and contained in a sealed package for a single use. When it is to be used, the sealed wet wipe package is torn open, and the single use moistened wipe removed, unfolded, and rubbed over the intended region of the skin. For large areas of skin several such wipes are needed, and it is a disadvantage that these typically include only a relatively small dose of repellent. An additional problem associated with many prior art applicators is that they are designed for and discarded after a single use. In addition to being economically disadvantageous, disposable applicators are environmentally troublesome. Further, should a user desire to make several separate applications during a day, for instance, a number of single use, multiple disposable applicators must be carried. Additionally aerosol spray cans of repellent can dangerously explode when left in a vehicle during the hot summer months, and pump-spray cans sometimes squirt excessively, causing repellent to drip about the skin, when overheated.

Many medical procedures involve the application of medicines, sterilizing fluids, antiseptics, gels, agents or other materials to portions of the body, such as the skin, for preparation, treatment, etc. Such medicines, sterilizing fluids, and similar agents are typically transferred to the skin via an applicator. Conventional liquid applicators may store liquids, and provide a sprayer function of some form for application. Alternatively liquid may be poured upon a swab, pad, or cotton-tip for subsequent direct topical application to the skin.

There are prior art attempts at containing various liquids and substances, such as cosmetics, for personal transportation and periodic discharge and application.

For example, U.S. Pat. No. 3,704,072 issued Nov. 28, 1972 discloses an analogous cleaning implement with enhanced scrubbing characteristics generated with the use of a cleansing compound or germicidal soaps. Action is generated with materials comprising a pored surface or a plurality of bristle-like elements, such as Velcro or brush bristles, that are used with a quantity of cleansing compound.

U.S. Pat. No. 4,148,318 issued Apr. 10, 1979 depicts an applicator tool for surgical preparations comprising an internal supply of antiseptic solution. The device has a reservoir from which and liquids may be applied to human skin with a sponge-like applicator element.

U.S. Pat. No. 4,269,527 issued May 26, 1981 discloses an applicator for pulverized substances. The applicator comprises a resilient container for pulverizable substance, a permeable membrane through which substances pass, and means for maintaining and releasing the pulverizable substance.

U.S. Pat. No. 4,557,620 issued Dec. 10, 1985 shows a cosmetic applicator which comprises a hand-sized storage container, a replaceable pad for applying the cosmetic, and a system of material carrying channels, a support screen, a flow limiter, a foam pad and a covering cloth.

U.S. Pat. No. 4,617,875 issued Oct. 21, 1986 discloses a grooming and treatment applicator with a circular housing for containing a liquid or powder for skin treatment, or insecticide, or a shampoo. Several alternative applicator face plates or heads are provided, with each having a brush, sponge, or other similar surface for engaging the hair, and with the face plates carrying nozzles extending for a distance substantially equal to the extremity of the brush or sponge, for example, and overlying the spaced openings.

U.S. Pat. No. 5,019,033 issued May 28, 1991 comprises a disposable, hollow bulb-shaped applicator with an ointment-permeable soft mesh membrane. Resilient walls surround and interconnect both ends of the applicator, and form a chamber for holding ointment. The ointment chamber may be filled by pressurizing the container (e.g. by squeezing) to force ointment from the container into the applicator.

U.S. Pat. No. 5,865,194 issued Feb. 2, 1999 provides a case for a cosmetic product in a powdery or semi-fluid form. The case has a rigid body, and a flexible bottom that define a variable volume compartment for containing product. The case also includes a fixed screen which allows the product to pass during simultaneous pressures on the flexible bottom and on the screen. The product can be a make-up or skin care powder.

U.S. Pat. No. 6,009,885 issued Jan. 4, 2000 discloses a powder puff case that permits face powder to directly and uniformly adhere to a powder puff through an adhesion net when turning upside down and shaking the powder case. Face powder directly and uniformly adheres through the adhesion net to the powder puff from the main body.

U.S. Pat. No. 7,201,525 issued Apr. 10, 2007 shows a solution applicator with a container, a head, and a cap. The head includes a top for use in applying the solution, a spike which pierces or opens a membrane, and at least one protrusion extending from the head. The head couples to a cap with complementary structure.

U.S. Pat. No. 7,866,907 issued Jan. 11, 2011 shows a medical skin applicator apparatus having a fluid chamber for storing a medical agent and an applicator coupled to the housing. The fluid housing has a penetrable wall to permit access to the fluid chamber and release of the medical agent. The applicator includes a surface for applying the medical agent to a patient.

U.S. Pat. No. 8,651,119 issued Feb. 18, 2014 shows a cosmetic case for a powder brush. A brush holder is rotated through a certain angle to an operational position to use the brush, and the brush may be taken out in an open state.

Other patents of possible interest include U.S. Pat. Nos. 1,318,256, 1,532,830, 1,553,049, 1,818,340, 2,919,703, 3,466,131, 3,704,072, 4,148,318, 4,269.527, 4,557,620, and 4,617,875.

SUMMARY OF THE INVENTION

This invention provides an applicator device with a self contained reservoir primarily for insect or bug repellents, such as liquid materials comprising DEET or the like, skin lotions and sunscreens.

The preferred invention comprises a handy and portable applicator for human use that uniformly applies insect repellent or sunscreen upon selected portions of skin. The applicator comprises a container that normally holds the liquid contents. The container may be threadably engaged by an upper, circular lid for closure. The lid functions as an applicator handle, but it may optionally include a separate handle portion. The lid supports a downwardly-projecting wiper, preferably comprising at least a portion of a sponge, that can be saturated with liquid for subsequent topical application of the applicator contents. The wiper contacts the underside of the lid, which may include flutes or channels for aiding liquid circulation.

In assembly, a coaxially disposed, wringer-saturator, preferably in the form of a circular, foraminous partition, is disposed between the liquid in the applicator, and the wiper for maintaining proper liquid flow. The wringer-saturator may be firmly positioned and supported upon a ring formed within the container. Alternatively the wringer-saturator may be disposed upon spacers or flutes. When the applicator is closed shut by the lid, the wiper is compressed slightly by contact with the wringer-saturator below it. As the lid is removed from the container, the wiper will expand slightly, ingesting liquid from within the container. Additionally, liquid may be further directed towards the wipe by channels or flutes in the lid underside. When the lid is tightly reattached, the wiper is compressed at least slightly against the wringer-saturator partition, "wringing" occurs, and liquid is at least partially expelled from the wiper.

Preferably the wiper is provided with a fabric or fiberglass covering that smooths the "feel" experienced by a user. Further, the covering helps to prevent dripping. In one form of the invention, the covering overlies the circular bottom and bottom periphery of the wiper. In alternate embodiments this covering may overlie and circumscribe a substantial length of the wiper, and in a preferred embodiment the covering shrouds the entire wiper exterior.

In the best mode the covering comprises fiberglass cloth, which has been found through experiment to provide excellent, drip free topical application and comfort, while at the same time minimizing unwanted dripping.

Thus a basic object is to provide a portable applicator for topical solutions such as bug/insect repellents, sterilizing substances such as rubbing alcohol, skin-care products, suntan creams or liquid preparations, and the like.

A similar object is to provide a reliable and comfortable topical applicator for a variety of insect or bug repellents, skin creams, cleansing and sanitizing substances, and suntanning products.

A fundamental object is to provide a repellent system for warding off bugs and insects, such as mosquitoes, flies, ticks including Lone Star ticks, triatomes (Chagas bugs) and the like.

Another primary object of the present invention to provide an applicator and enclosure that is readily adapted to function advantageously with a number of different liquid gels and blends that are adapted to function as insect repellents, germicides, skin creams, and/or sunscreens.

It is a further object of the present invention to provide a repellent applicator/container that is easily used and transported.

Another object is to make it easy to contain and apply bug repellents with sunscreens. Another object is to provide an applicator that minimizes the potential mess often associated with spray dispensers.

A related object is to provide an applicator of the character described that facilitates the accurate and precise placement of desired quantities or amounts of product.

Another object is to provide a container with a removable lid that doubles as a hand-held applicator tool for the precise topical coating of product upon the human skin.

A basic object is to provide an applicator for insect repellent for humans and animals for protecting against a diverse array of insects and pests.

A collateral object is to provide a repellent applicator system of the character described that contains germicidal liquids that are toxic to germs and viruses such as the H1N1, Sars, and novel Covid-19 viruses.

It is also an object of my invention to provide a dispenser of the character described that is safe, effective and easy to use.

These and other objects and advantages of the present invention, along with features of novelty appurtenant thereto, will appear or become apparent in the course of the following descriptive sections.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views:

FIG. 11 is a partially exploded, elevational assembly view of the applicator of FIGS. 9-10; with portions thereof broken away for clarity; and.

DETAILED DESCRIPTION OF THE SEVERAL VIEWS OF THE DRAWINGS

Figure 1:
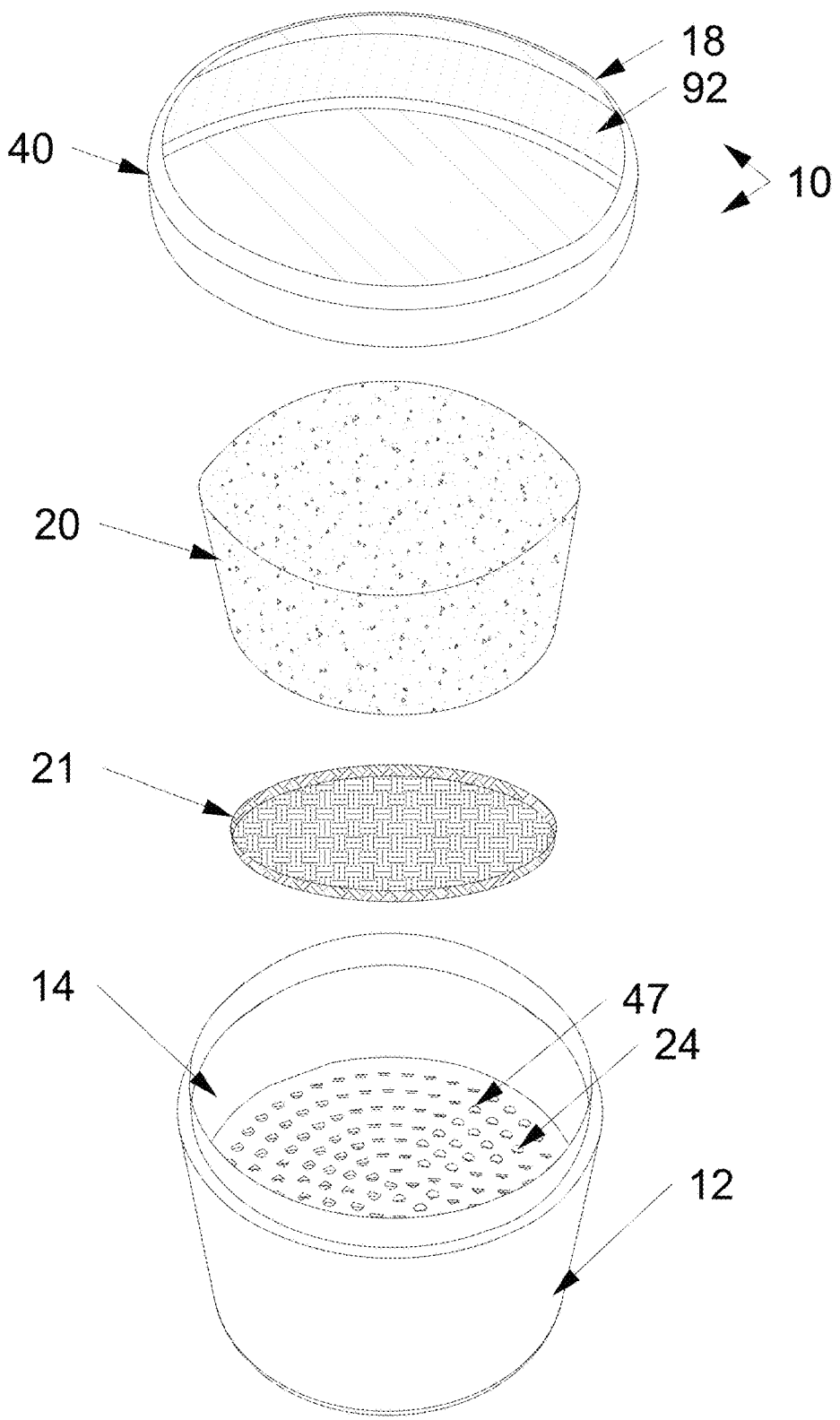
FIG. 1 is a partially exploded, isometric assembly view of a first applicator embodiment constructed in accordance with the teachings of the invention.

With initial reference now directed to FIGS. 1-5 of the appended drawings, an insect repellent applicator constructed in accordance with the a preferred mode of the invention has been generally designated by the reference numeral 10. There are multiple embodiments known at this time discussed hereinafter.

Figure 4:
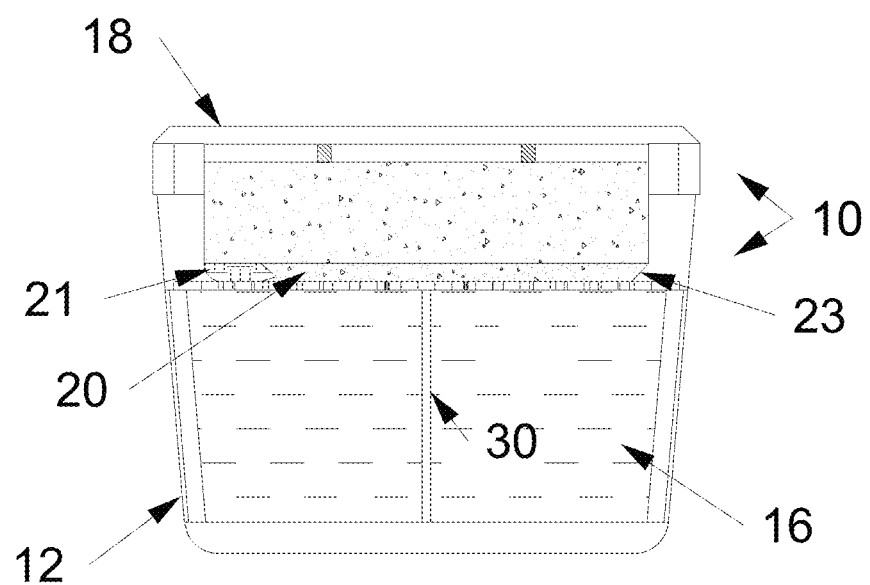
FIG. 4 is an enlarged, fragmentary longitudinal sectional view of the applicators of FIGS. 1-3.
Figure 5:
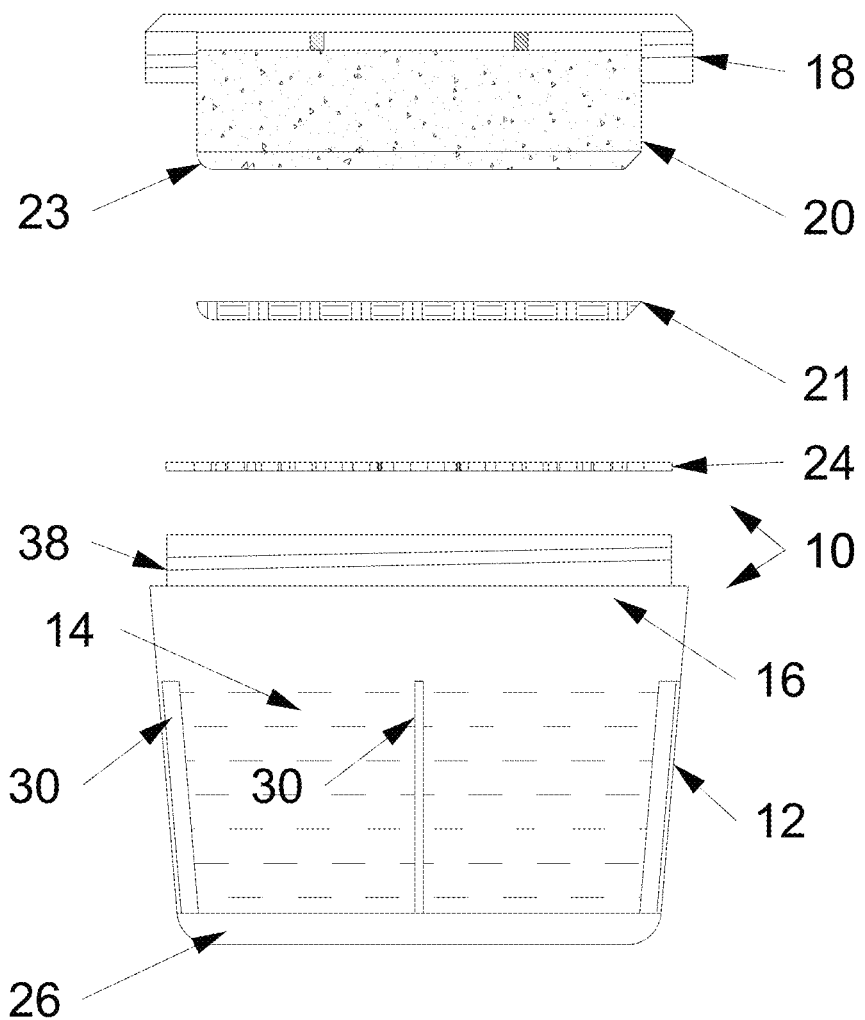
FIG. 5 is an exploded longitudinal sectional view of the applicator of FIGS. 1-4, with portions thereof shown in section for clarity.

Applicator 10 comprises a jar-like, preferably glass container 12 defining an interior 14 adapted to contain various liquids or substances to be used with the invention. These substances include liquids or creams of various viscosities, including as insect repellents, gels, suntan lotions, sterilizing agents, or disinfectants. In FIG. 4 the liquid contents of the applicator 10 has been generally designated by the reference numeral 16.

A substantially circular lid 18 is adapted to be threadably secured to the container 12 for closure. Lid 18 supports a downwardly projecting wiper 20 that is preferably concentrically positioned at and secured to the lid bottom, and which projects downwardly into the container interior 14. Preferably there is a thin, light-weight covering 21 shrouding at least the circular periphery 23 (FIG. 2) and the bottom of wiper 20. The covering 21 is preferably fabricated from fabric material, but fiberglass fabric is preferred.

The lid 18 once removed from the container 12 can function as a handle for applying the container contents. In other words the lid 18 may be grasped while rubbing the wiper 20 upon the skin. However, the lid 18 may optionally include a separate, integral handle portion 92 (FIG. 1).

There is a wringer-saturator 24 preferably in the form of a circular, foraminous partition 24 that can contact and at least partially compress wiper 20. The wringer-saturator is secured beneath the lid 18 within the interior 14 of the container jar 12. As explained hereinafter, the wringer-saturator partition 24 functions as a wringer and saturator in operation.

Container 12 is preferably of substantially cylindrical construction, and is preferably made of glass or plastic. Alternative shapes and sizes are within the purview of the invention. The container has a lower reinforced base 26 adapted to be disposed upon a supporting surface for stowage. A plurality of radially spaced apart, interior ribs 30 (FIG. 2) integral with the container 12 extend vertically upwardly within the container. The ribs 30, which may be disposed approximately 120 degrees apart about the radial inner periphery of the container 12, provide support for the wringer-saturator partition 24 which is pressed unto them in assembly. Preferably the length of each interior rib 30 is approximately ⅔ of the height of the container 12. The upper, reduced diameter hub portion 38 (FIG. 2) of the container 12 is threaded, enabling coupling to the lid 18 in assembly.

The preferred removable lid 18 comprises an integral, concentric, rim 40 whose inner peripheral surface 44 is threaded. In operation lid 18 with rim 40 functions as a handle for applying fluids. This enables the lid 18 to be threadably attached to the container 12, by engagement with the complimentary, threaded hub 38. When the lid 18 is threadably tightened to the jar 12, the downwardly projecting wiper 20, supporting a lower, peripheral fabric covering 21, is compressed slightly against the wringer-saturator partition 24 disposed in between. If the liquid level within the jar is full, then slight contact with the wiper 20 and liquid through the partition is established. The covering prevents dripping during use. Moreover, with the fiberglass version of the covering, the human body experiences a smooth and gentle feeling when the wiper is drawn or rubbed softly over the skin.

Wiper 20 is generally cylindrical with an exterior surface, and may have somewhat the shape of a truncated cone. Preferably the wiper is made from plant-based or synthetic sponge material, and it is resistant to corrosive chemicals. The wiper 20 may be other shapes. For example it may be generally cylindrical in shape with a circular or oblong or oval or square cross section. Preferably wiper 20 extends concentrically from the bottom of the lid 18, to which it may be fastened by gluing or the like. Wiper 20 is used for topical application of liquids within the jar to the region or areas requiring treatment with insect repellent. Applicator wiper 20 is "squashed" or compressed against the wringer-saturator partition 24 in assembly, but it will will expand and hold liquid when released from compression by loosening the jar lid 18.

When the wiper 20 is compressed against the wringer-saturator partition 24, it will exhibit a "wringer" effect, wherein liquid that would otherwise be stored within it is squeezed out from pressure. The liquid also passes through wiper covering 21 that shrouds the bottom of wiper 20 and its bottom radial periphery 23. On the other hand, when the lid is slowly threadably twisted for removal, the wiper 20 will expand slightly and suck in liquid for subsequent topical application, becoming somewhat saturated with liquid. Covering 21 aids in liquid retention when the lid is removed. The preferably sponge wiper 20 will substantially retain liquids when in use, and will thus prevent or reduce dripping and messiness when in use.

Figure 2:
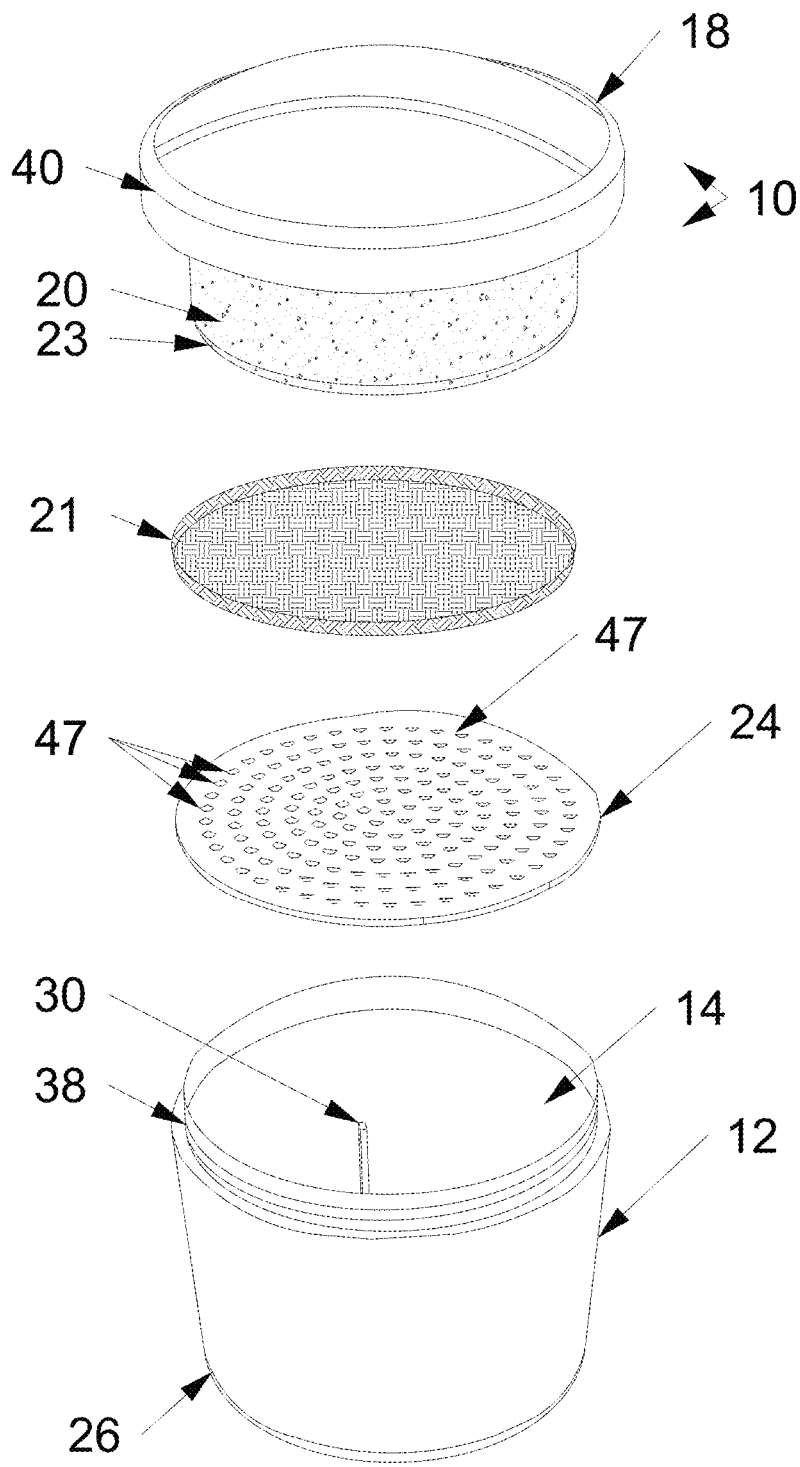
FIG. 2 is a partially exploded isometric assembly view of the applicator of FIG. 1.
Figure 3:
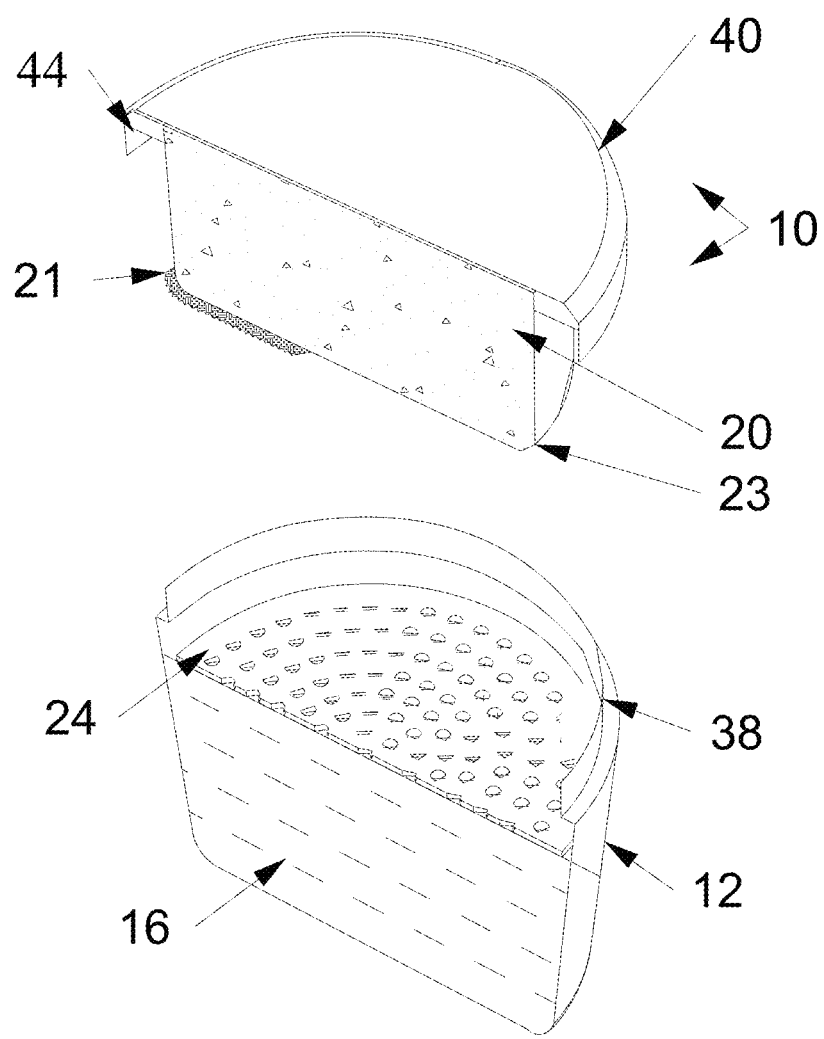
FIG. 3 is a fragmentary, partially exploded isometric view of the applicator of FIGS. 1-2, with portions thereof shown in section for clarity.

The preferred thin covering 21 on the bottom of wiper 20 surrounds at least the the wiper exterior bottom periphery 23 (FIG. 2). In the preferred embodiment the shrouds the entire periphery of the wiper. This substantially circular covering 21 may be made from thin, fabric or garment materials such as polyester or linen, but preferably fiberglass. Covering 21 concentrically shrouds the bottom radial periphery 23 (FIG. 2) of the rim of the wiper 20 and the wiper's bottom surface. In use, the wringer 20 with its thin covering 21 ergonomically slides over exposed ski, and easily glides over all bony surfaces such as ankles, wrists, knees, etc.

The preferred wringer-saturator partition 24 is substantially circular, and is concentrically positioned within the container 12, being supported within the jar interior upon the upper tips of the interior ribs 30. The wringer-saturator partition 24 includes numerous orifices 47 for allowing controlled liquid passage between the jar interior and the wiper 20. The wringer-saturator partition 24 functions as a combination wringer/saturator. When the wiper 20 is compressed against the wringer-saturator partition 24, the effect is that of a wringer, with solution being squeezed out of the wiper 20. When the jar lid 18 is withdrawn from the jar, then the action of removal allows the wiper 20 to expand, drawing liquid into it and partially through covering 21, with the wiper 20 becoming saturated. While the lid is removed slowly by twisting, and with slight shaking of the container 12, the wiper 20 will become maximally saturated with liquid for subsequent topical application.

Figure 6:
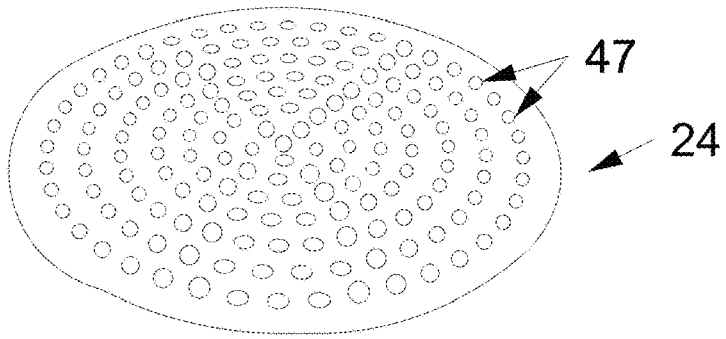
FIGS. 6-8 are enlarged isometric views of alternative wringer-saturator partitions.

The preferred wringer-saturator partition 24 includes a plurality of orifices 47 as mentioned. These orifices are preferably square or circular, although other geometries are possible, and are within the scope of the invention. The combined area of the partition orifices 47 (i.e., FIG. 6) is approximately twenty to sixty percent of the area of the partition, depending upon the viscosity of the interior gel fluid or repellent 16. Preferably there is a conventional peripheral gasket 49 defined about the outer circular periphery of the wringer-saturator partition 24, which facilitates firm seating of the partition when it is press-fitted within the jar interior.

In the best mode known at this time, the lid 18, the wringer-saturator partition 24, and the container 12 may be molded from ultra-high molecular weight polyethylene (UHMWPE) plastic. It is thought that other thermoplastic materials may be used, as long as they do not dissolve or degrade when subject to the liquid contents. For example, PTFE (polytetrafluoroethylene) is a softer plastic that has excellent chemical resistance properties. A durable resin that emulates HDPE is acceptable for most fluids.

Figure 7:
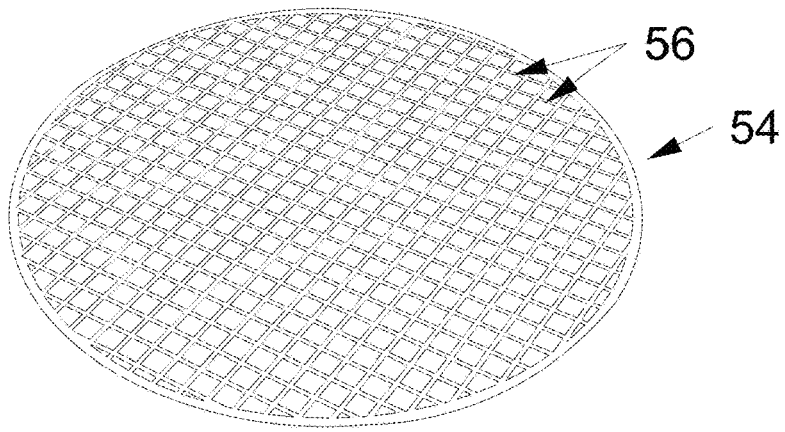

FIG. 7 shows an alternative wringer-saturator partition 54 that includes multiple orifices 56. However, this embodiment contemplates that the orifices 56 have a square profile. The combined area of the square partition orifices 56 (i.e., FIG. 7) is approximately ten to forty percent of the area of the partition 54, depending upon the viscosity of the interior fluid repellent 16.

Figure 8:
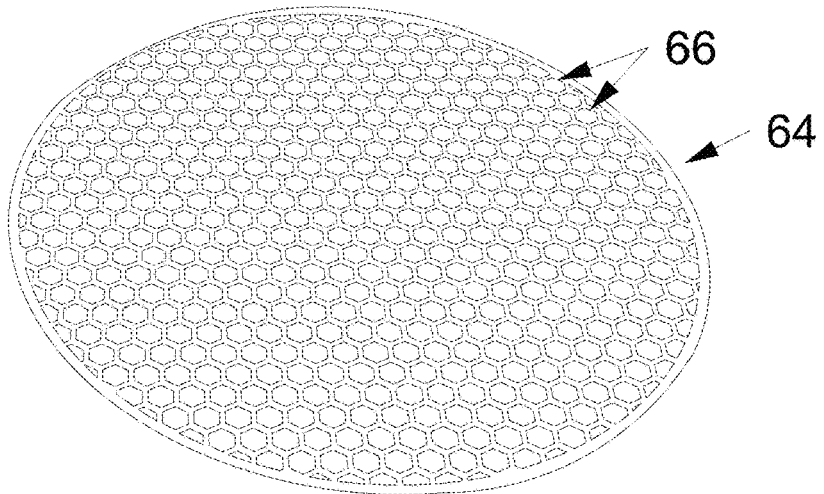

FIG. 8 shows another wringer-saturator alternative partition 64 that includes multiple honeycomb orifices 66. The combined area of the partition orifices 66 (i.e., FIG. 8) is approximately ten to forty percent of the area of partition 64, depending upon the viscosity of the interior fluid 16. Numerous other partition shapes may be used.

Figure 9:
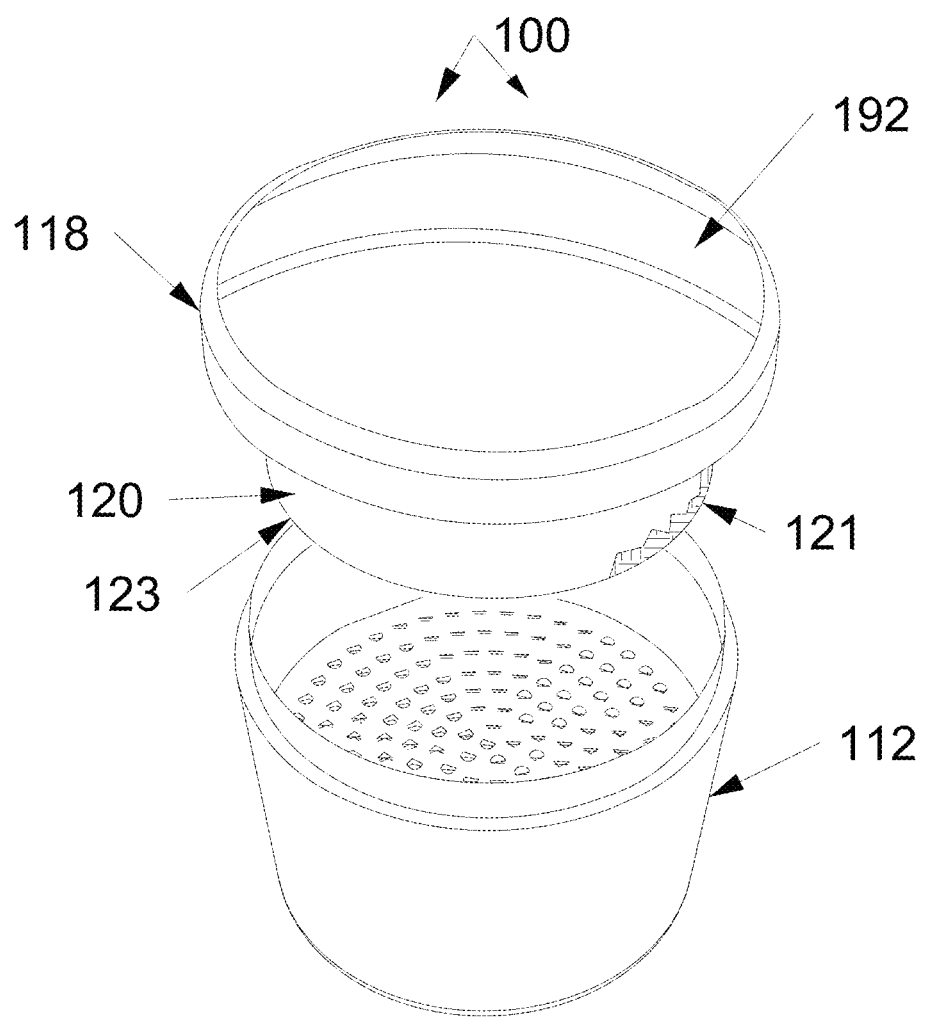
FIG. 9 is a partially exploded, isometric assembly view of a preferred applicator that has an enhanced wiper, with portions thereof broken away for clarity.
Figure 10:
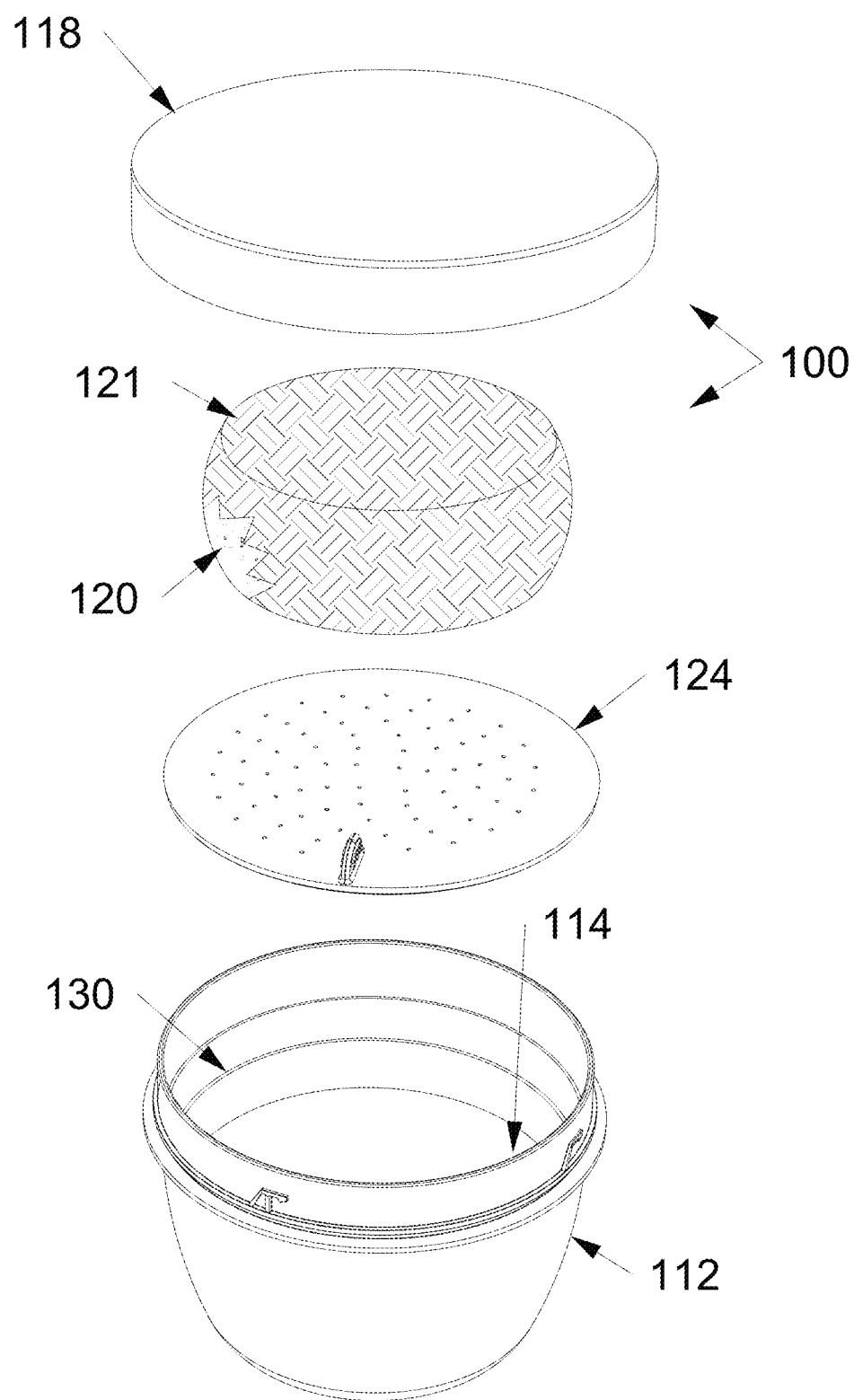
FIG. 10 is an exploded isometric view of the applicator of FIG. 9, with portions thereof broken away for clarity.
Figure 11:
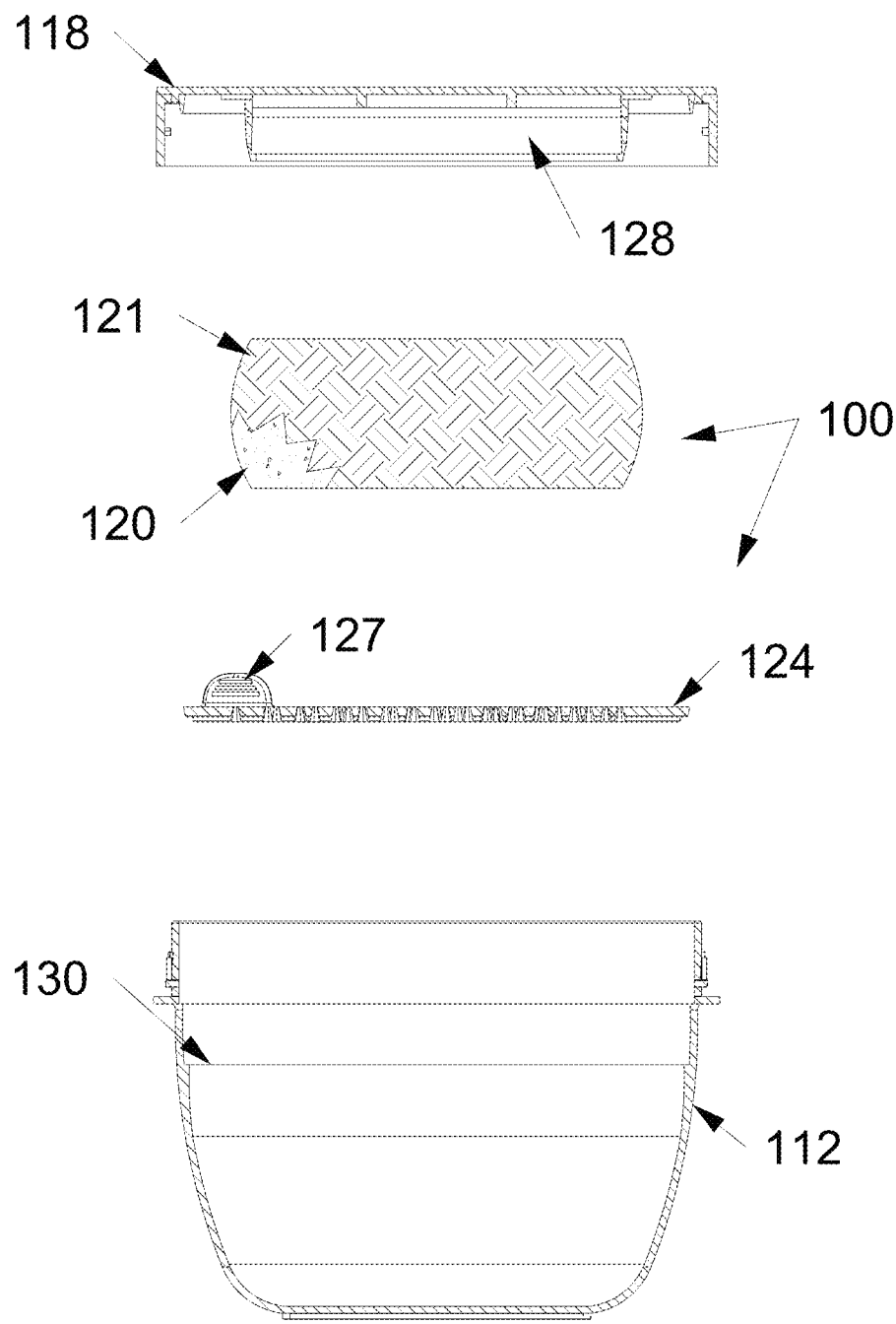

Referencing FIGS. 9-11, a preferred embodiment of an applicator 100 has a different wiper covering than applicator 10 discussed earlier. The substantially circular lid 118 is adapted to be secured to the container 112 for closure. A sponge wiper 120 concentrically fastened to the lid bottom projects downwardly into the container interior 114. Wiper 120 is substantially similar to wiper 20 discussed earlier, except for the cover 121. The shrouding cover 121 may overly parts of the exterior surface of the wiper 120, or the entire exterior. Thus, while covering 21 (FIG. 1) shrouds just the lower the bottom circular periphery of wiper 20, covering 121 preferably shrouds most, if not all, of the exterior surface of wiper 120 as seen in FIG. 10. Covering 121 is preferably fabricated from fiberglass fabric material.

In applicator embodiment 100, the lid 118 may optionally include a separate, integral handle portion 192 (FIG. 9).

Figure 12:
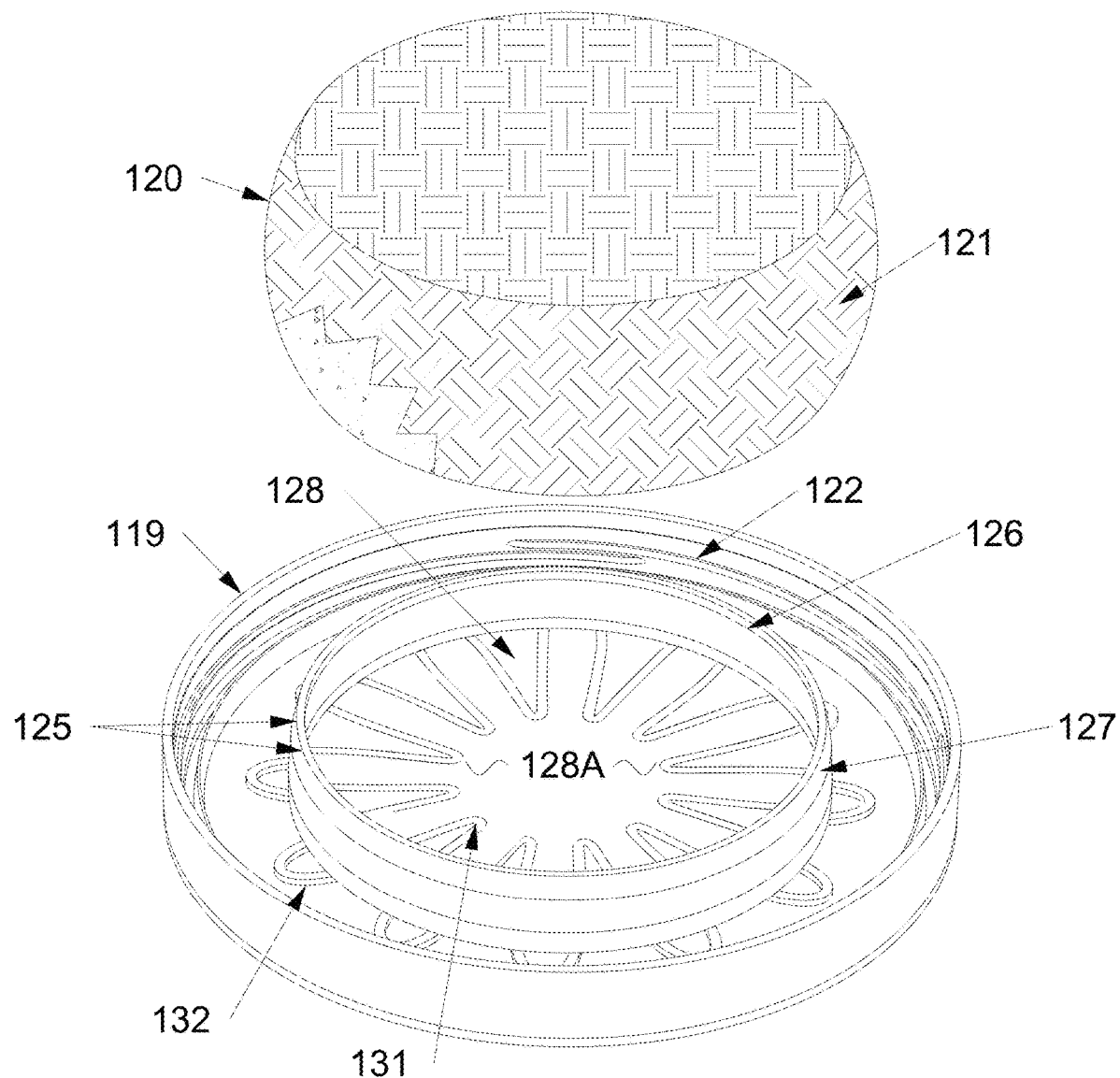
FIG. 12 is an enlarged, exploded isometric view showing a preferred wiper and the underside of the preferred lid which has been adapted to center and secure the wiper.

Noting FIG. 12, a preferred lid 119 has an integral, interior, projecting mounting ring 125 concentrically formed on its underside 128. (In FIG. 12 ring 125 appears to be projecting upwardly because the lid 119 is upside down.) This somewhat tubular ring 125 surrounds an inner wiper-mounting region 128A forming the center of the lid underside. The inner periphery of the lid's rim includes threads 122. The wiper 120 may be glued to the lid underside 128 and cradled upon and within wiper-mounting region 128A, being confined therewithin by contact with the periphery of ring 125, and by contact with reinforcing lip 127 and adjacent, inner compression band 126 on the ring 125. The wiper 120 may be fastened by gluing to the lid underside upon region 128. Surrounding region 128 (FIG. 12) are a plurality of inner raised channels 131 and outer, complimentary raised channels 132 that both reinforce the lid and increase the contact area for proper wiper-to-lid contact and more complete glue bonding.

The channels 131 and 132 have an appearance resembling a flower petal, and their three dimensional character insures more reliable glue bonding by the wiper. Furthermore, these raised channels with their petal construction can control and help circulate liquid to the wiper, particularly more viscous liquids including bug repellents and sunscreen preparations, which tend to cling to the lid underside, preventing over-saturation of the wiper, and dripping therefrom. Depending upon the orientation of the applicator 100, liquid can be directed upon the upper portion of the wiper 120 when the applicator 100 is returned to an upright position after being substantially upside down. Preferably the wiper 120 is made from plant-based or synthetic sponge material, and it is resistant to corrosive chemicals. Alternatively, the wiper may be made from other synthetic materials including fabric designs.

Wringer-saturator 124, which is similar to wringer-saturator 24 (FIG. 1) discussed earlier, contacts and at least partially compresses wiper 120. The wringer-saturator 124 is secured within the container 112 atop an inner rim 130 (FIG. 10) formed integrally with the container 112. Also, the wringer-saturator 124 includes an integral, upwardly projecting lip 127 (FIG. 11) that enables grasping and manipulation tasks when necessary for cleaning or maintenance.

The interior liquid repellent or gel 16 (i.e., FIGS. 3, 4) normally fills the jar interior up until contact with an internal partition. The liquid 16 contains insect repellent in a one to ten percent by volume mixture. With sufficient viscosity the liquid 16 is absorbed by the wiper 20 through the orifices in the previously described partitions. The lid is then manually grasped and with wiper contact upon the skin of a user, for example, the repellent liquid may be evenly and cleanly spread upon a target area. At this time the best mode known to me for liquid 16, by weight, is a mixture as follows:

20-50% N,N-diethyl-m-toluamide (DEET)
40-70% ethyl alcohol
6-7% Aloe
3-4% fragrance or perfume Another example of a suitable liquid repellent mixture comprises a transparent insect repellent containing N,N-diethyl-m-toluamide (DEET), water, a solvent selected from a variety of lower alcohols including glycols, isopropyl alcohol, or ethanol, a gelling agent, methyl and propyl paraben, a perfume for masking the odor of the DEET, and a means for improving and stabilizing the texture of the liquid or gel 16. For the latter ingredient a polysorbate, preferably polyoxyethylene sorbitan monolaurate, is preferred for improving the texture of the gel.

Yet another example of a suitable repellent mixture is as follows:
a) from two to ten percent by volume a liquid containing N, N-diethyl-m-toluamide (DEET);
b) from forty to sixty percent by volume denatured water;
c) from thirty to seventy percent by volume a solvent selected from alcohols including glycols, isopropyl alcohol, or ethanol;
d) from two to ten percent by volume a stabilizer;
e) around five percent, an emollient skin cream.

Moreover, the invention works with common over-the-counter bug sprays and sun screens. For example, it has been successfully used with the following: OFF! family care insect repellent IV; OFF! defense insect repellent 2 with picaridin; OFF! botanicals insect repellent IV; Cutter Skinsations Insect Repellent; Babyganics natural insect repellent; Bug Soother with Lemongrass Oil; Neutrogena Ultra Sheer Face mist sunscreen spf 55; Neutrogena Invisible Daily defense face mist spf 50; Hawaiian Tropic AntiOxidant+ refresh sunscreen mist spf 30; and Bondi Sands The Australian Tan liquidgold self-tanning dry oil Coconut Scent.

A variety of traditional guidelines and/or instructions exist for the use of DEET-based products. Basic instructions known in the art are as follows:
1. The container should be held six to eight inches from skin or clothing, and application should employ a gentle sweeping motion.
2. Do not apply over cuts, wounds or irritated skin.
3. Do not apply in enclosed areas or inside the home; always do so outdoors.
4. Use just enough repellent to treat all exposed areas of skin.
5. Avoid over applicating the product. After applying product to exposed skin, evenly spread the product with a gentle rubbing by the hands to maximize protection.
6. Do not allow children to handle the product, and do not apply to children's hands. When using on children, apply to your own hands and then spread the product on the child.
7. Hands should be washed with soap and water after every application.
8. After applying to the palms of hands, products may be distributed upon and around the neck, ears, and face, while avoiding the eyes and mouth.
9. Do not spray product around or near food.
10. Always wash hands with soapy water before eating or drinking when wearing repellent even if there has been no recent application.
11. No children ten years old or less should apply bug repellents or sunscreen. These substances should be applied to children only by adults.
12. When using a spray or pump, no one should breathe the vapors.

Conversely, use of the instant applicator/dispenser eases the burden on the user. Steps like spraying the product, rubbing it in with the hands and having to follow-up by washing the hands, which are often inconvenient and bothersome for many outdoor consumers. There are a large number of users that carelessly streak the product and do not follow other recommendations to spread it with the hands to attain total coverage of exposed skin that guarantees maximum protection. Unfortunately, some users actually avoid use of any repellent products because of spraying and application inconveniences.

Finally, the importance of periodic reapplication of bug repellents and/or sunscreens cannot be emphasized enough. Reapplication is markedly critical every two to four hours on a long outing. With old fashioned spray cans and pumps, for example, periodic reapplication is largely ignored and/or omitted. Preventing toxicity from toxic bites and ultraviolet light becomes greatly simplified with my new applicator/dispenser. With the use of the instant invention, the traditional guidelines discussed above can be relaxed dramatically.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations.

As many possible embodiment's may be made of the invention without departing from the scope thereof, it is to be understood that all matter herein set forth or shown in the accompanying drawings is to be interpreted as illustrative and not in a limiting sense.

What is claimed is:

1. An applicator for use with substances to be topically applied to the body, the applicator comprising:
a generally cylindrical container adapted to at least temporarily hold said substances, the container comprising an interior and a height, and the container comprising a predetermined diameter;
a lid adapted to be removably secured to the container for closure, the lid functioning as a handle when removed from said container;

a downwardly projecting wiper attached to the lid and concentric with said container for absorbing or dispensing said substances, the wiper having a periphery, wherein said wiper is made from sponge material which is resistant to corrosive chemicals, and the wiper comprising a diameter less than said container diameter;

a fiberglass covering shrouding at least a portion of the wiper periphery for preventing dripping during use and ergonomically easing substance application, wherein the covering is made from glass fiberglass material;

a wringer-saturator disposed within said container that divides said interior and which at least slightly contacts said wiper when said cover is firmly attached to said container, said wringer saturator comprising a plurality of orifices through which said substances may pass;

wherein the container comprises means for interiorly supporting said wringer-saturator;

whereby, when said lid is attached to said container, the wiper slightly compresses against said wringer saturator , and when the lid is removed the wiper expands slightly and further absorbs at least a portion of said substances, so that the wiper may thereafter contact the body to apply said substances, with said covering preventing dripping and ergonomically smoothing the feel of the applicator with the sponge wiper.

2. The applicator as defined in claim 1, wherein the combined area of the said wringer saturator orifices is approximately twenty to sixty percent of the area of the wringer saturator.

3. The applicator as defined in claim 1, wherein the wringer saturator comprises multiple honeycomb orifices.

4. The applicator as defined in claim 3, wherein the combined area of the wringer-saturator orifices is approximately ten to forty percent of the area of the wringer saturator.

5. An applicator for topically applying low-viscosity substances to the human body, the applicator comprising a generally cylindrical container adapted to at least temporarily hold said substances, the container comprising an interior and a height and a predetermined diameter;

a lid adapted to be secured to the container for closure, the lid functioning as a handle when removed from said container, and the lid comprising a bottom;

a sponge wiper projecting concentrically downwardly from the lid bottom for absorbing or dispensing said substances; the wiper having a lower peripheral rim and an exterior and a predetermined diameter less than said container diameter;

a fiberglass covering shrouding the wiper exterior for preventing dripping during use and easing substance application;

a wringer-saturator disposed within said container that divides said interior and which at least slightly contacts said wiper when said lid is firmly attached to said container, said wringer saturator comprising a plurality of orifices through which said substances may pass;

wherein the wringer-saturator is molded from ultra-high molecular weight polyethylene (UHMWPE) plastic;

whereby, when said lid is attached to said container the wiper slightly compresses against said wringer-saturator and absorbs at least a portion of said substance , and when the lid is removed the wiper expands and retains at least a portion of said substances, so that the wiper may thereafter contact the body to apply said substances, with said fiberglass covering in cooperation with said sponge wiper preventing dripping and ergonomically smoothing the feel of the applicator, with compression of said wiper against the human skin facilitating substance discharge.

\* \* \* \* \*